United States Patent [19]

Davis et al.

[11] Patent Number: 5,059,680

[45] Date of Patent: Oct. 22, 1991

[54] METHOD OF ISOLATING CA 125 ANTIGEN

[75] Inventors: Hugh M. Davis; Thomas L. Klug; Vincent R. Zurawski, Jr., all of Westchester, Pa.

[73] Assignee: Centocor, Inc., Malvern, Pa.

[21] Appl. No.: 933,784

[22] Filed: Nov. 24, 1986

[51] Int. Cl.[5] .......................... C07K 15/00; C07K 3/28
[52] U.S. Cl. .................................... 530/350; 530/395; 530/412; 530/413; 530/417; 530/418; 530/419; 530/420; 530/827; 530/853; 530/832; 530/387; 435/70.1; 424/85.8
[58] Field of Search ............... 530/350, 395, 827, 853, 530/832, 387, 412–413, 417–420; 435/70.1

[56] References Cited

U.S. PATENT DOCUMENTS 4,584,278 4/1986 Knauf .................................... 435/7

OTHER PUBLICATIONS

Nouwen et al., *Canacer Res.*, 46, 1986, pp. 866–876.
Hanisch et al., *Eur. J. Biochem.*, 149, 1985, 323–330.
Klug et al., *Cancer Res.*, 44, 1984, pp. 1048–1053.
Mastropado et al., *Clin. Chem.*, 32(11), 1986, pp. 2110–2111 (abst. only).
Shimizu et al., *Nippon Sonku Fujinka Gabhai Zarshi*, 37(R), pp. 2813–2820, 1985 (abst. only).
Davis et al., *Cancer Research*, 46:1–6 (Dec., 1986).
Kabawat et al., *American Journal of Clinical Pathology*, 79(1):98–104 (Jan., 1983).
Kabawat et al., *International Journal of Gynecological Pathology*, 2:275–285 (1983).
Bast et al., *Journal of Clinical Inventigation*, 68:1331–1337 (Nov., 1981).
Masuho et al., *Cancer Research*, 44:2813–2819 (Jul., 1984).
Bast et al., *The New England Journal of Medicine*, 309:883–887 (Oct., 1983).

*Primary Examiner*—Garnette D. Draper
*Attorney, Agent, or Firm*—Hamilton, Brook, Smith & Reynolds

[57] ABSTRACT

A preparation of an isolated immunoreactive CA 125 Antigen, and a method of isolating it is disclosed. CA 125 Antigen is a glycoprotein having a molecular weight of about 200kD, and a carbohydrate-content of about 24%. The CA 125 Antigen is isolated from a cell culture medium by acid precipitation, and is subsequently purified by size exclusion chromatography and immunoaffinity chromatography.

20 Claims, 4 Drawing Sheets

METHOD OF ISOLATING CA 125 ANTIGEN

BACKGROUND

CA 125 is a tumor-associated antigen expressed on greater than 80% of all non-mucinous ovarian epithelial tumors of serous, endometrioid, clear cell and undifferentiated histologies. Bast, R. C., Jr. et. al., *J. Clin. Invest.* 68:1331–1337, 1981; Kabawat, S. E. et. al., Am. J. Clin. Pathol., 79:98–104, 1983. The murine monoclonal antibody OC125 which reacts with CA 125 was generated by use of an established human serous cystadenocarcinoma cell line, OVCA 433. Bast, R. C., Jr. et. al., supra. Quantitation of this determinant in serum of patients with ovarian cancer has been made possible by the development of an immunoradiometric assay with OC125. Klug, T. L. et. al., *Cancer Res.*, 44:1048–1053, 1984. The CA 125 antigenic determinant has also been reported to be found in human milk (Hanisch, F. G. et. al., *Eur. J. Biochem.*, 149:323–330, 1985.), in normal cervical mucous (de Bruijn, H. W. A. et. al., *Am. J. Obstet. Gynecol.*, in press) and in the central airway and normal lung tissue (Nouwen, E. J. et. al., *Cancer Res.*, 43:866–876, 1986). In addition, CA 125 activity appears to exist in human seminal plasma.

The CA 125 determinant has been reported to be associated with a mucin-like high molecular weight glycoprotein complex. See e.g., Hanisch, F. G. et. al., *Eur. J. Biochem.*, 149:323–330, 1985; Niloff, J. M. et. al., *Am. J. Obstet. Gynecol.*, 151:981–986, 1986; Bast, R. C. et. al., *Ovarian Cancer*, pp. 23–35, Boston, Mass.: Martinus Nihofi, 1985; Masuho, Y. et. al., *Cancer Res.*, 44:2813–2819, 1984; and Bast, R. C., Jr. et. al., *Cancer Bull*, 37:80–81, 1985. However, the lack of a procedure for isolation of CA125 antigen has impaired analysis of its chemical composition.

DISCLOSURE OF THE INVENTION

This invention pertains to a method of isolating the antigen CA 125, to preparations of the isolated antigen and to methods of using the isolated antigen.

The CA 125 antigen can be isolated in high purity as a 200 kDa species from tissue culture medium of ovarian carcinoma cells which "shed" the antigen into the growth medium, (e.g. the human serous cystadenocarcinoma cell line OVCA 433). The CA125 species isolated by the procedure described herein is the same as the species of CA125 found in the serum of patients with non-mucinous ovarian carcinoma, as determined by electrophoretic and immunoblotting analysis.

According to the procedure of this invention, the cell free supernatant is obtained from a culture of human ovarian carcinoma cells. In a first step, protein is precipitated by acid treatment (e.g. perchloric acid, 6M) and the precipitated protein is removed. The acid soluble fraction which contains the CA 125 activity is then neutralized.

CA125 activity in the acid soluble fraction is associated with a high molecular weight complex ($>1,000,000$ Da). In the next step, molecular size exclusion chromatography is then used to separate this high molecular weight CA125 species from lower molecular weight components. For example, the acid soluble fraction can be applied to a column of Sepharose TM 4B-CL gel. The Sepharose TM 4B-CL retains molecules of about 60,000–2,000,000 Da. The CA 125 complex is eluted from this column in the void volume.

A chaotropic agent (e.g. Urea, 6M) is used to disrupt the high molecular weight CA 125 complex separated by molecular size exclusion chromatography. The chaotropic agent can be added to the CA 125-containing fraction from the Sepharose TM 4B-CL column. The CA 125 is then separated by a second molecular size exclusion chromatography step. This column is chosen to retain a 200, kDa CA125 species (e.g. Sepharose TM 6Bresin). The chromatography is performed with an elution buffer containing the chaotropic agent and a detergent (e.g. SDS) to stabilize the disrupted CA125. The retained fractions containing CA 125 activity (as determined reactivity with OC125 antibody) are collected as they are eluted from the column. The chaotropic agent is removed from the collected fraction e.g. by dialysis.

In the final step of the isolation procedure, the CA 125 is immunopurified using OC125 antibody. For this purpose, an immunoaffinity column comprising immunoactive OC125 coupled to a resin material (e.g. Sepharose 4B) is used.

The CA125 antigen isolated by this procedure has a molecular weight of about 200kDa and a buoyant density of about 1.36 g/ml. The antigen is 24% carbohydrate (by mass). Antibody binding (OC125) activity is heat and protease labile but exoglycosidase and periodate insensitive, indicating that the cognate determinant of OC125 is likely to be proteinaceous.

Isolated CA 125 antigen can be used to raise polyclonal or monoclonal antibody reactive with CA 125. Antibody against OC125 can be used in diagnosis and/or therapy of ovarian carcinoma. e.g. tumor imaging, passive immunotherapy, and immunotoxin therapy. Further, the isolated CA 125 antigen can be used for detection of anti-CA 125 antibody (e.g. by solid phase RIA or ELISA) in the serum, plasma or other biological fluids of patients. The presence of anti-CA 125 antibody in a patient may provide an indication of the existence or recurrence of ovarian carcinoma.

DETAILED DESCRIPTION OF THE INVENTION

Figure 1:
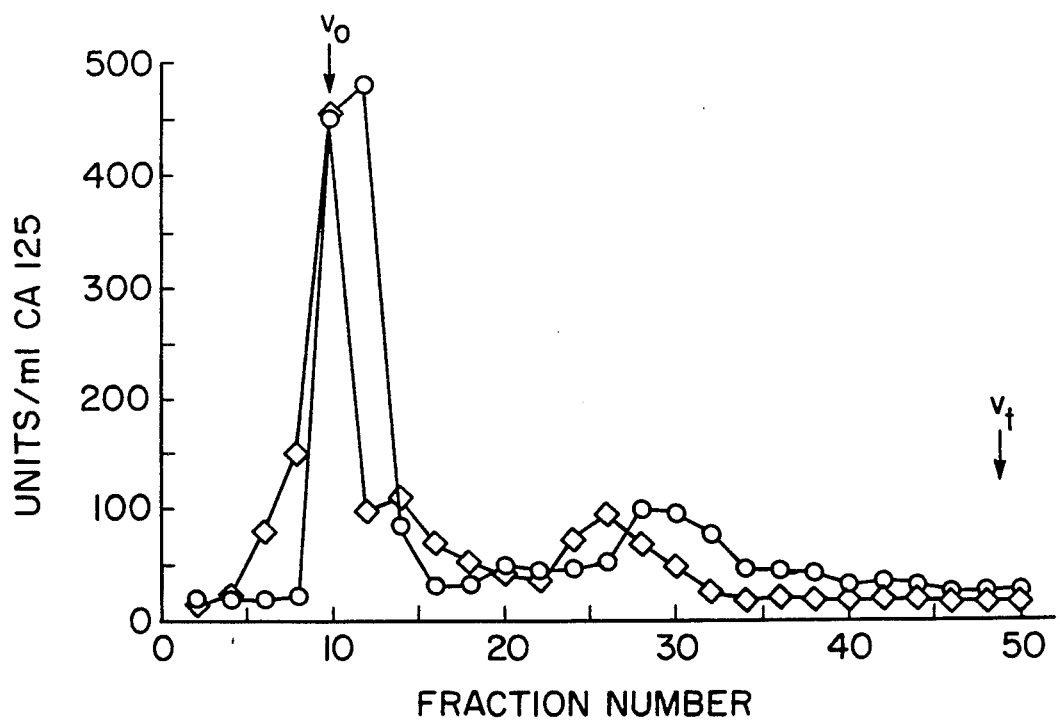
FIG. 1 is the elution profile on Sepharose CL-4B column chromatography of the CA 125 antigen isolated from OVCA 433 tissue culture supernatant (       ) and from human serum (       ).

The procedure for purifying CA125 generally entails four steps, as indicated below. The procedure can be applied to isolate CA125 from tissue culture media in which ovarian carcinoma cells have been grown. The cells, of course, must be ovarian carcinoma cells which express the antigen and "shed" (release) the antigen into the growth medium. The procedure may also be used to isolate the antigen from biological fluids such as serum or ascites. However, the minute quantities found in these fluids generally make them an impracticable source of the antigen for purification.

The preferred ovarian carcinoma cell line is the OVCA 433 cell line described by Bast, R. C., Jr. et al., supra. Other cell lines which can be used are the ovarian tumor cell lines NIH:OVCAR-3 (ATCC #HTB161), SK-OV-3 (ATCC # HTB77), CAOV-3 (ATCC # HTB75), and CAOV-4 (ATCC # HTB76). When grown in a conventional tissue medium, these cell lines release CA125 antigen into the medium. The released antigen can then be isolated from the medium by the four step procedure.

1. Acid Precipitation

Cell-free supernatants are subject to acid precipitation. The preferred acid is perchloric acid at 0.6M final concentration. Precipitated protein is removed and the acid soluble fraction which contains the CA125 activity is neutralized (e.g. with KOH). The acid soluble fraction can then be dialyzed against distilled water and concentrated (e.g. 20× original supernatant volume).

2. Molecular Size Exclusion Chromatography

The acid soluble fraction is submitted to molecular size exclusion chromatography to separate the high molecular weight CA125 complex from lower molecular weight components. A preferred resin is Sepharose CL-4D resin which retains molecules in the α kD to 2,000 kD range. The CA125 antigen is eluted from this column in the void volume. The antigen can be applied and eluted in phosphate buffered saline (PBS)

3. Treatment with Chaotropic Agent and Molecular Size Exclusion Chromatography The fraction containing CA125 activity is treated with a chaotropic agent. The chaotropic agent disrupts the high molecular weight CA125 complex. Urea is preferred, but quanidine-HCl may also be used. Urea treatment is followed by chromatography with a resin that retains molecules in the 200 kD range. A preferred resin is Sepharose CL-6B. The chromatography on Sepharose CL-6B is done with a buffer containing the chaotropic agent (e.g. 6M Urea) and a detergent (e.g. 1% SDS). The eluted fraction can be monitored for CA125 activity by CA125 RIA.

4. Affinity Purification

The CA125 antigen is purified by immunoaffinity chromatography. OC125 is bound to a solid phase (e.g. Protein A-Sepharose Cl-4B resin) and the antigen containing fraction from the prior gel filtration step is passed over the resin under conditions which allow the antigen to bind specifically to the solid phase. The antigen is then eluted with an appropriate eluant such as diethylamine. The preferred immunoaffinity column is prepared essentially by the methods of Schneider et. al., infra. OC125 is covalently coupled to Protein A-Sepharose via the coupling agent dimethylsimelimidate, a coupling which does not interfere with the activity of the OC125 antibody. Bound antigen is eluted with diethylamine.

In the preferred embodiment, CA 125 antigen is purified from OVCA 433 cell culture supernatants using the procedure described below.

Purification Step 1. Cell culture supernatants from OVCA 433 culture are collected from confluent monolayer cultures. Supernatants are concentrated 10 fold and made 0.6 molar in perchloric acid. Precipitated protein is removed. The acid soluble fraction is neutralized, and then dialyzed against distilled water. The CA 125 reactivity is found in the soluble fraction (95%), while 80% of the protein is removed.

Purification Step 2. The perchloric acid soluble fraction is concentrated and fractionated by gel filtration chromatography using a 3.2×85 cm column of Sepharose TM 4B-CL equilibrated in phosphate buffered saline (PBS). CA 125 activity and $A_{280}$ are determined for each fraction. The majority of CA 125 activity is eluted at the void volume (Vo) and a smaller peak which elutes later. This profile indicates the presence of a high molecular weight component (>1000 kDa) and a smaller component (200 to 400kDa). The Vo fractions contain about 85% of the initial reactivity.

Purification Step 3. The Vo fraction from the Sepharose 4B-CL column is made 6M in urea and then applied to a 1.2×95 cm Sepharose 6B-Cl column in 0.1% SDS, 6M urea, 50 mM Tris HCl, pH 8.0. Fractions are collected and assayed for CA 125 reactivity. The CA125 activity is eluted in two peaks: Peak 1, a minor, high molecular weight component (>1000 kDa) at the void volumne and Peak 2, a major, lower molecular weight component (200 to 400 kDa).

Purification Step 4. The material is peak 2 is further purified by immunoaffinity chromatography. An affinity column is prepared by covalently coupling OC125 antibody to a Protein A-Sepharose 4B-CL column according to the method of Schneider et. al. The pooled Peak 2, still in 6M urea, 0.1% SDS, is passed over the immunoaffinity column three times. After washing, the antigen is eluted with 50 mM diethylamine (DEA) pH 11.5. The eluate is immediately neutralized by collection into a neutralizing buffer, and is then dialyzed against distilled water.

The antigenic activity of CA 125 at each step of this purification has been evaluated using Western blots. Most of the reactivity from Purification Step 1 (PCA extraction) has a very high molecular weight (>1000 kDa), and little or no reactivity is found in the low molecular weight region (<1000 kDa). Analysis of the peak 2 from Purification Step 3 indicates that most of the reactivity is in the 200–400 kDa region. This suggests that the 1000 kDa antigen dissociates into a smaller component. Finally, in Purification Step 4, the antigen eluted from the immunoaffinity column has the 200–400 kDa component with no detectable 1000 kDa reactivity.

To demonstrate that the 200–400 kDa components noted after Steps 3 and 4 were formed by dissociation of the >1000 kDa material, Western blots were performed on a PCA extract, with and without treatment with 6M urea. The untreated PCA extract had a major component of 1000 kDa and a minor 200–400 kDa component. After treatment with 6M urea (45° for 30 minutes), most of the reactivity was found in the 200–400 kDa region.

The isolation procedure of this invention can give a 3900-fold purification relative to starting supernatant material (as determined by activity in units/mg protein in starting material versus final material). The CA125 antigen species isolated by this procedure is characterized by the following:

It has a molecular weight of about 200 kDa. It is comprised of 24% carbohydrate. The carbohydrate composition is sialic acid, fucose, mannose galactose, N-acetyl-glucosamine, and N-acetyl galactosamine in the ratio 3.6/0.4/3.0/6.6/5.8/2.2.

The region of the OC125 determinant appears to be proteinaecous (See exemplification below).

The isolated immunoreactive 200 KDa species of CA 125 can be used as an immunogen preparation to raise anti-CA 125 antibody. For example, monoclonal anti-CA125 antibodies can be produced by standard techniques of Kohler and Milstein. A mouse is immunized with the isolated CA125. Spleen cells are harvested and fused with myeloma cells. Resulting hybridomas can be selected for anti-CA 125 antibody production on the basis of reactivity with isolated CA 125 antigen.

Antibody against CA 125 is useful for diagnosis and therapy of ovarian carcinoma. For example, the antibody can be used in diagnostic tests such as RIAs and ELISAs for the presence of CA 125 in biological fluids. Such antibody can be used in immunohistochemical techniques for identification of tumor. techniques for identification of ovarian carcinoma cells. The antibodies may also be used for in vivo imaging of ovarian cancer and for immunotherapy of ovarian cancer e.g. passive immuno therapy or immunotoxin therapy.

The isolated CA 125 can also be used to provide an immunoadsorbent for detection of anti CA125 antibody in the blood. The presence of CA125 antibody may provide an indication of ovarian carcinoma in a patient.

The invention is illustrated further by the following exemplification.

EXEMPLIFICATION

Materials and Methods

Materials

The murine monoclonal antibody OC125, produced by hybridomas grown in pristane primed BALB/c mice (Bast, R. C. et. al. *J. Clin. Invest.*, 68:1331–1337, 1981), was isolated by protein A chromatography (Kabawat, S. E. et. al. *Am. J. Clin. Pathol.*, 79:98–104, 1983). Serum samples were obtained from women with advanced epithelial ovarian cancer (stage III and IV). Human milk was obtained from a healthy 7-month post partum female. The exoglycosidases and proteases were purchased from Calbiochem, Los Angeles, Calif. (pronase), and from Sigma, St. Louis, Mo. (chyxotrypsin, trypsin, chondroitinase ABC, α-and β-galactosidase, α-fucosidase, hexaminidase, and neuraminidase). Monoclonal antibody 1116NS 19-9 (Koprowski, H. et. al. *Somat. Cell Genet*:5(6):957–972, 1979; U.S. Pat. No. 4,349,528) was obtained from Dr. Zenon Steplewski, Wistar Institute, Philadelphia, Pa. Polyclonal anti-CEA antibody was obtained from Abbott Laboratories, North Chicago, Ill. Sepharose CL-4B and CL-6B and Protein A-Sepharose CL-4B were purchased from Pharmacia, Piscataway, N.J. Electrophoresis reagents were purchased from Bio-Rad, Rockville Centre, N.Y. SeaKem LE agarose was purchased from FMC Corp., Rockland, Me. Fish gelatin was obtained from Norland Products Inc., New Brunswick, N.J. All other reagents were of the highest purity commercially available.

Solid-Phase Radioimmunoassays

The simultaneous "sandwich" immunoradiometric assay (IRMA) was used to measure CA 125 activity (Klug, T. L. et. al. *Cancer Res.*, 44:1048–1053, 1984.) and CA 19-9 activity (Ritts, R. E. et. al. *Int. J. Cancer*, 33:339–445, 1984). In the CA 125 IRMA, [$^{125}$I]—OC125 (100 ul, $1 \times 10^5$ cpm) was incubated (20 h, 23° C.) with polystyrene-immobilized OC125 and sample (100 ul). The beads were washed ($3\times$) and counted in a gamma counter. Assay kits were manufactured at Centocor, Malvern, Pa.

The plate assay was performed using 96 well polyvinyl chloride microtiter plates (Dynatech). The OVCA 433/PCA/4B (see "Isolation of CA 125 from OVCA 433 tissue culture supernatants") fraction was used to coat the wells (100 ul, 500 units/well). Following the binding of the antigen to the plates (18 h, 4° C.), the wells were incubated for 1 h with phosphate buffered saline (PBS) containing 5% (w/v) bovine serum albumin. After the incubation period, the wells were emptied and washed ($2\times$) with PBS. [$^{125}$I]-OC125 (20 ul, $2 \times 10^4$ cpm) was then incubated with the immobilized antigen (4 h, 23° C.). The wells were subsequently washed ($3\times$) with PBS, cut, and counted in a gamma counter.

As the CA 125 IRMA only detects polyvalent antigens, an inhibition assay was developed to quantitate both mono- and multi-valent antigens. The inhibition assay was performed similarly to the plate assay described above, the only difference being that [125I]-OC125 (20 ul, $2 \times 10^4$ cpm) was incubated simultaneously (30 ul, 4 h, 23° C.) with various antigen preparations which might inhibit binding of radiolabeled OC125 to the plate. The wells were washed ($3\times$), cut, and counted in a gamma counter. The radioiodinated OC125 used in both the plate and inhibition assays was obtained from Centocor RIA kits.

SDS:Polyacrylamide Gel Electrophoresis

Conventional SDS:PAGE was performed essentially according to the method of Laemmli (Laemmli, U.K. *Nature* 227:680–685, 1970.). The sample buffer did not contain sulfhydryl reducing agents or SDS and was not heated, as the CA 125 antigen was inactivated by these conditions. Some experiments required a polyacrylamide-agarose composite gel for separation of sample components as the CA 125 antigen did not penetrate a conventional 3% (w/v) polyacrylamide gel.

Typically, the composite gels were prepared with 2.5% polyacrylamide and 1.0% agarose. The solutions were heated to 65° at which time the ammonium persulfate was added. The prewarmed solutions were then immediately poured into the gel apparatus which had been equilibrated at 37° C. and the entire apparatus was then cooled at 4° C. until the agarose solidified. After overlaying a 2.5% polyacrylamide-1.0% agarose stacking gel at room temperature the samples (300 units/lane) were applied in 10M urea sample buffer which did not contain sulfhydryl reducing agents or SDS and was not heated. The electrophoresis was performed at 4° C. All buffers used in the preparation and running of the composite gels were also those of Laemmli (See supra.).

Immunoblotting

After electrophoresis the proteins were electrophoretically transferred to nitrocellulose (Towbin, et al., *Proc. Natl. Acad. Sci.* 76:4350–4354, 1979)), immunoblotted with radiolabeled OC125, and autoradiographed. Each immunoblot contained at least one negative antigen control lane. The electrophoretic transfer was performed at 100 mA overnight. Immunoblotting was accomplished by overlaying the nitrocellulose with radioiodinated OC125 (2 ml, $2 \times 10^6$ cpm) in fish gelatin buffer (1% fish gelatin, 50 mM citrate, pH 6.0, 0.05% NP-40) for 6 h. The nitrocellulose sheet was then autoradiographed by exposure to x-ray film with the aid of a Cronex Quanta III fluor screen (Dupont) for 18 h at $-80°$ C.

Fractionation of Human Serium and Human Mild

Whole serum was allowed to clot for 1 h and then centrifuged ($3,000 \times g$, 10 min). A portion (2 ml) of the supernatant was fractionated on a $1.2 \times 47$ cm Sepharose CL-4B column (human serum/4B) equilibrated in PBS. Fractions (1 ml) containing CA 125 activity, as determined by the CA 125 RIA, were pooled and concentrated. Human milk was defatted by centrifugation ($3,000 \times g$, 1 h) at 10° C. The supernatant was further purified by column chromatography as described above for serum (human milk/4B).

Preparation of CA 125 Antigen Concentrate from OVCA 433 Tissue Culture Supernatant OVCA 433 human ovarian carcinoma cells were grown in Minimum Essential Medium Eagle supplemented with 2 mM glutamine, 1 mM pyruvate, 1% non-essential amino acids, and 10% heat-inactivated fetal calf serum. T-150 flasks (Costar) were seeded with $1 \times 10^6$ cells. Growth was permitted to continue until cells reached confluence at which time the medium was removed. Fresh medium was added and collected at 5–7 day intervals, for a total of 10–12 weeks. OVCA 433 cells appeared to produce the maximum amount of CA 125 antigen in $G_0$ growth phase. The cancellation of CA 125 antigen produced under these conditions was approximately 1,000 units/ml. Pooled cell supernatants were centrifuged at $10,000 \times g$, filtered through a Sartorius 0.2 micron pore size cascade filter capsule, and concentrated to one-tenth the original volume with an Amicon DC-2 hollow fiber apparatus and filter cartridge (HP 100-200) with a molecular weight cutoff of 100 kDa. The concentrates were stored frozen at $-20°$ C. under which conditions the CA 125 activity was stable for at least 12 months.

Isolation of CA 125 from OVCA 433 Tissue Culture Supernatant

The spent tissue culture $10\times$concentrate of the OVCA 433 cell supernatant was first subjected to perchloric acid (PCA, 0.6M final concentration) precipitation (Krupey, J. et. al. *J. Exp. Med.* 128:387-398, 1968). The CA 125 activity remained in the PCA soluble fraction and was completely conserved. The acid soluble fraction was neutralized with potassium hydroxide (1.2M), dialyzed against distilled water (24 h, 4° C.), and concentrated to $20\times$ the original supernatant volume. This sample is referred to as OVCA 433/PCA. The OVCA 433/PCA sample (35 ml) was applied to a Sepharose CL-4B column ($3.2 \times 70$ cm) equilibrated in PBS. The fractions (7 ml) which contained CA 125 activity as determined by the CA 125 RIA were pooled and concentrated. This fraction is referred to as OVCA 433/PCA/4B and is used in all experiments except as indicated.

Further fractionation involved treatment of the OVCA 433/PCA/4B fraction with urea (6M, 30 min, 45° C.) and subsequent chromatograph on a Sepharose CL-6B column equilibrated in Tris-urea-SDS (50 mM Tris, 6M urea, 0.1% SDS, pH 8.0). Final fractionation was accomplished by immunoaffinity chromatography on an OC125-Protein A-Sepharose CL-4B column. The monoclonal antibody OC125 was covalently bound to the Protein A-Sepharose CL-4B column, washed and coupled essentially according to the method of Schneider et al., *J. Biol. Chem.* 257:10766–10769, 1982. Minor modifications included the substitution of citrate buffer (0.05M, pH 6.0) for Tris-HCl, and taurodeoxycholate (TDC) for deoxycholate (DDC). Repeated passes ($3\times$) over the affinity column of the CA 125 reactive lower molecular weight fraction from the Sepharose CL-4B column in 0.1% SDS and 6M urea gave greater than 80% binding of the CA 125 activity. Elution of the CA 125 antigen from the column was accomplished with the use of diethylamine (DEA) (50 mM, pH 11.3). This affinity purified antigen is referred to as OVCA 433/4B/DEA.

Density Gradient Ultracentrifugation

Ultracentrifugation of the CA 125 antigen isolated either from human serum, human milk, or from the OVCA 433 tissue culture supernatant after chromatograpy on Sepharose CL-4B was performed in a cesium chloride isopycnic density gradient in PBS (2.276 g of CsCl dissolved in 3.414 ml of PBS). The buoyant density of B-galactosidase was determined as a standard. Fractions (0.2 ml) were assayed for B-galactosidase activity following equilibrium by the method of Miller (*Experiments in Molecular Genetics*, Cold Spring Harbor Laboratory, Cold Spring Harbor, N.Y., 1972). Gradients were formed by ultracentrifugation in a Beckman SW50.1 rotor (33,000 rpm, 68 h, 10° C.) under conditions which have been described (See, Magnani, J. L. et. al., *Cancer Res;* 43:4589–5492, 1983). Fractions (0.2 ml) were collected and assayed for activity using the CA 125 RIA described above. The density of each fraction was determined by weighing a known volume.

Chemical Treatments

Periodate oxidation of the CA 125 antigen was accomplished with 0, 0.1, 1.0, 10.0 and 100 mM periodate in acetate buffer (pH 4.5, 50 mM, 4° C.) in the dark according to Stahl et al., *Proc. Natl. Acad. Sci;* 73;4045–4049, 1976. Reduction and alkylation were performed according to methods described elsewhere. See, Glazer, A. N. et. al., Chemical Modifications of Proteins. In: T. S. Work and E. Wbrk/Eds) *Laboratory Techniques in Biochemistry and Molecular Biology,* p. 104, New York:Elsevier Publishing Co., 1975. Reduction was accomplished with DTT (10 mM, 50 mM Tris, pH 8.1, 4 h, 45° C.) either in the presence or absence of guanidine-HCl (6M). Alkylation was performed with iodoacetic acid (20 mM, 30 min) after the samples had been cooled to room temperature. The samples were immediately dialyzed (4° C., 18 h) against distilled water.

Exoglycosidase Treatments

Exoglycosidase digestions were performed in acetate buffer (0.01M, pH 4.5, 48 h, 37° C.). Unit values of the exoglycosidases were chosen in order to ensure complete digestion of the oligosaccharide residues within an appropiate time frame. All exoglycosidase digestions were performed under conditions whereby the appropriate substrates were shown to be completely hydrolyzed as detected by thin layer chromatography. CA 125 activity following treatment was measured both by the CA 125 RIA and by the plate assay as previously described.

Exhaustive Protease Digestion

The various protease digestions were performed in Tris-HCl buffer (0.2M, pH 8.0, 10 mM calcium chloride). The proteases trypsin, chymotrypsin, and pronase (2% w/v, 50 ul) were added to wells containing antigen and allowed to incubate (48 h, 37° C.). Protease digestions were performed under conditions which caused hydrolysis of albumin as detected by thin layer chromatography. Samples were assayed for CA 125 activity by both the CA 125 RIA and the plate assay as described above.

Amino Acid Analysis

Samples of OVCA 433/4B/DEA were dissolved in 6N HCl containing 0.1% phenol, sealed under vacuum, and hydrolyzed for 24 h at 110° C. Amino acids were derivatized with phenylisothiocyanate (PITC) and derivatized PTC-amino acids separated and quantitated by HPLC using the Waters PICO-TAG column and elution conditions See Bidlingmeyer, B. A. et. al. *J. Chromatogr.*, 336:93–10$^4$ (1984).

Carbohydrate Composition

Samples of the same lot of OVCA 433/4B/DEA that had been subjected to amino acid quantitation were subjected to carbohydrate compositional analysis as described by Yang and Hakomori, *J. Biol. Chem.* 246:1192–1200, 1971. The samples were subjected to acetolysis, followed by hydrolysis and reduction. The resultant alditols were per-O-acetylated with acetic anhydride. Quantitation of sialic acid was accomplished by trimethylsilyl derivatization (TMS). Laine, R. A. et. al., *Meth. Enzymol.* 28:159–167, 1972. Both the alditol acetate and the TMS-methyl glycosides were separated by a Hewlett Packard 5790 gas chromatograph and identified by a Hewlett Packard 5790 mass selective detector (MSD).

RESULTS

Physical and Immunological Characteristics of the CA 125 Antigen

The antigen isolated from OVCA 433 and from human ovarian cancer patient serum by perchloric acid precipitation elutes primarily in the void volume of a Sepharose CL-4B column (FIG. 1). In addition, a smaller peak of CA 125 activity elutes from the column later indicating a much lower molecular weight. These peaks of CA 125 activity correspond to molecular masses of greater than 1,000 and about 200–400 kDa. The CA 125 antigen elution pattern of human milk is similar to that shown for OVCA 433 and human cancer patient serum.

Figure 2:
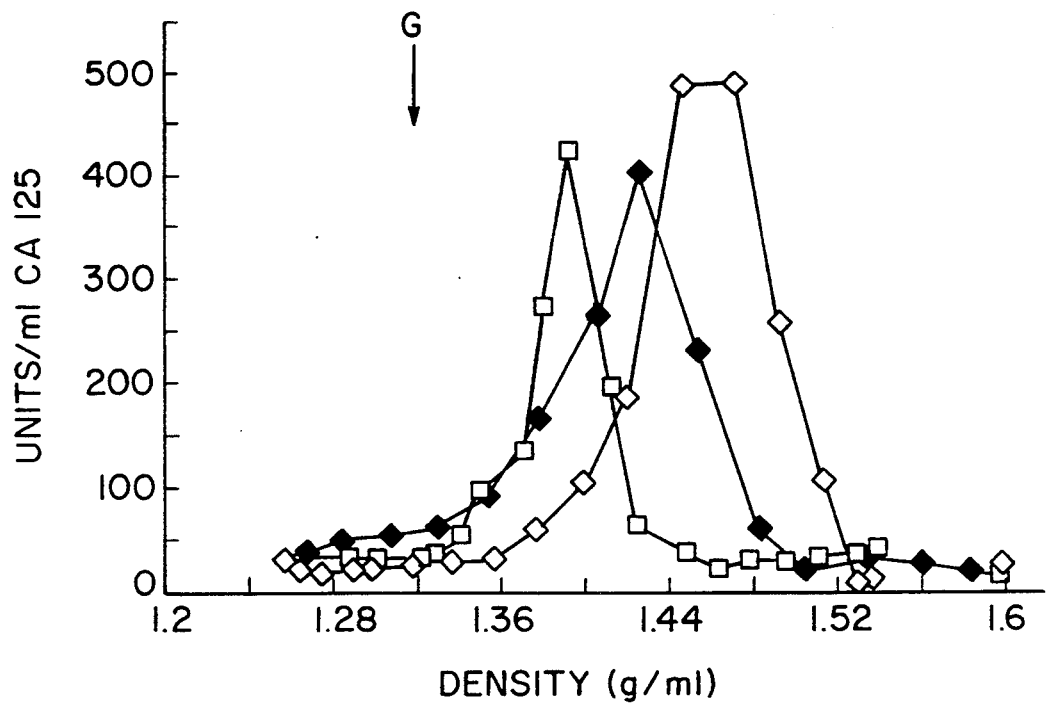
FIG. 2 shows density gradient ultracentrifiguation centrifugation following Sepharose CL-4b column chromatography of the CA 125 antigen isolated from human serum (       ), OVCA 433 tissue culture supernatant (       ), and from human milk (       ).
Figure 3:
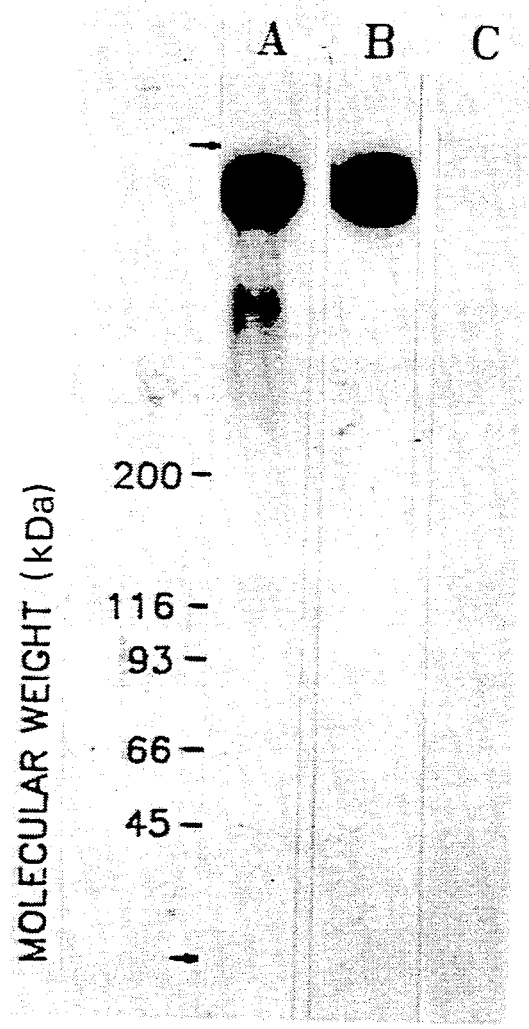
FIG. 3 shows conventional SDS:PAGE (3–12% gradient) of CA 125 antigen isolated from OVCA 433 followed by immunoblotting.
Figure 4A:
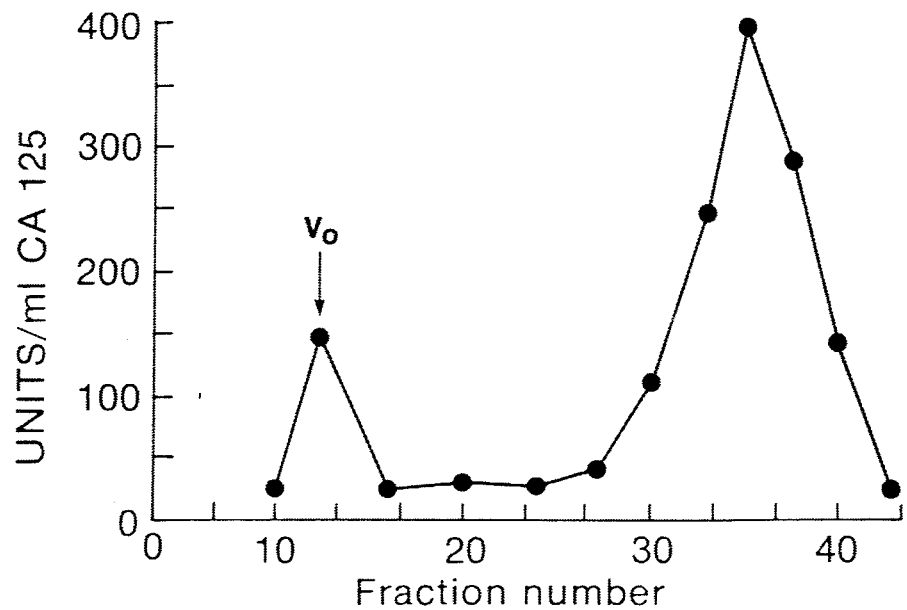
FIG. 4A shows Sepharose CL-6B elution profile of the CA 125 antigen isolated from OVCA 433. Elution was performed in a SDS-urea-Tris buffer following treatment in 6M urea at 45° C. for 30 min. Fractions were assayed for-CA 125 activity with a solid-phase RIA.
Figure 4B:
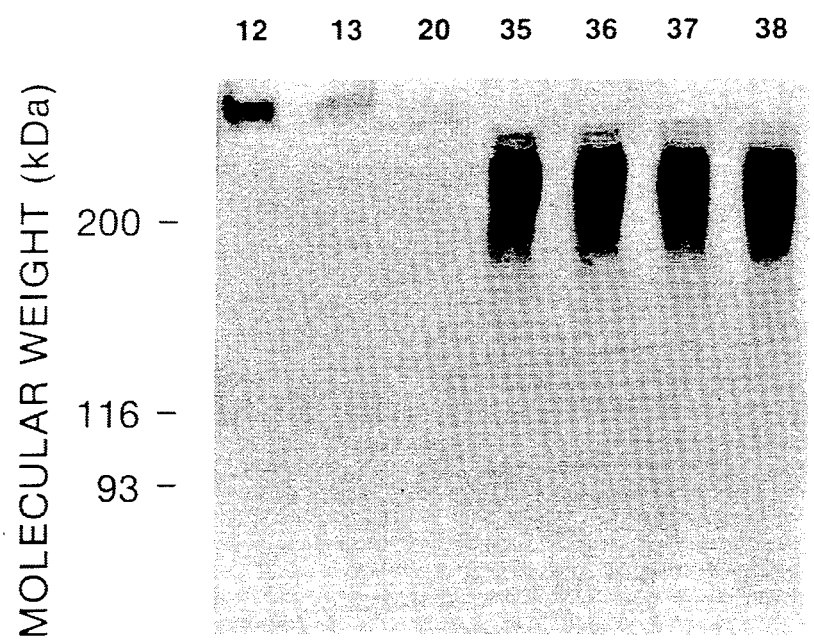
FIG. 4B shows the SDS:PAGE (6%) of pertinent fractions of the Sepharose CL-6B gel filtration column chromatography.

In an effort to compare the physical characteristics of the antigen isolated from OVCA 433 cell supernatants, ovarian cancer patient serum, and human milk, a buoyant density was determined for each (FIG. 2). The average buoyant density of the antigen isolated from OVCA 433 after passage over a Sepharose CL-4B column (OVCA 433/4B) is approximately 1.42 g/ml whereas the buoyant densities of the patient serum/4B and the milk/4B are 1.46 and 1.39 g/ml, respectively. As a standard, the buoyant density of >-galactosidase was determined and found to be 1.32 g/ml. This agrees well with the published value of 1.316 g/ml Costini, N. V. et. al., *J. Biol. Chem;* 254:11242–11246, 1979. The electrophoretic mobility of immunoreactive species from OVCA 433/4B, human milk/4B, and ovarian cancer serum/4B on a composite 2.5% polyacrylamide/1.0% agarose gel was compared. The samples were applied in 10M urea sample buffer which did not contain DTT or SDS and was not heated. The immunoblotted OC125 reactive antigen from each of the sources is present as high molecular mass complexes of between 200 and 1,000 kDa with similar electrophoretic profiles. This data, which suggests multiple aggregated states of the CA 125 antigenic complex, correlates well with the Sepharose CL-4B elution profile shown in FIG. 1. Both experiments indicate that antigen exists as a high molecular mass species of greater than 1,000 kDa and lower molecular mass species of approximately 200–600 kDa When the OVCA 433/PCA/4B fraction is subjected to SDS:PAGE electrophoresis using a 3–12% polyacrylamide gradient gel followed by immunoblotting (FIG. 3), the lane which is reactive with radioiodinated monoclonal antibody OC125 give rise to a band of greater than 1,000 kDa molecular mass and a lower molecular mass band of approximately 400 kDa. The sample buffer used contained only 10% glycerol, 0.08M Tris, pH 6.8, and bromophenol blue. After overlaying the adjacent lane with radioiodinated monoclonal antibody 19-9, which recognizes the sialylated lacto-N-fucopentaose II carbohydrate determinant, only the higher molecular mass band is observed. The lane which is overlaid with radioiodinated anti-CEA does not shown any immunoreactivity. Furthermore, Western blots using monoclonal antibody 19-9 as an overlay with the OC125 affinity purified CA 125 antigen (OVCA 433/4B/DEA) fraction does not give rise to any bands. Also, there is no CA 19-9 activity present when measured by the CA 19-9 RIA (data not shown). This result clearly demonstrates that the antigenic determinants CA 125 and CA 19-9 are located on the same high molecular mass glycoprotein complex, but the CA 125 and CA 19-9 determinants are not present on the same glycoprotein molecule The results of Sepharose CL-4B column chromatography and of SDS:PAGE analysis suggests that the lower molecular weight material was probably derived from the higher molecular weight species. Attempts to disaggregate the high molecular weight material with both ionic (SDS) and non-ionic (NP-40) detergents proved futile. However, treatment of the pooled and concentrated void volume fraction of the Sepharose CL-4B column of OVCA 433/PCA with 6M urea for 30 min at 45° C., followed by column chromatography on Sepharose CL-6B in 0.1% SDS and 6M urea yields two peaks, as shown in FIG. 4. Following this step, the majority (80%) of the CA 125 activity is found associated with a much lower molecular mass peak of approximately 200 kDa. This is verified by electrophoresis and immunoblotting of fractions from the Sepharose CL-6B column chromatography (FIG. 4). Some of the antigen still remains in the high molecular mass aggregated form.

Immunoaffinity Purification of the CA 125 Antigen from OVCA 433 Cells

Sepharose CL-4B column chromatography followed by treatment with 6M urea and heat with subsequent column chromatography on Sepharose CL-6B in the presence of 6M urea and 0.1% SDS (FIG. 4) results in a 1,400-fold purification of CA 125 antigen from OVCA 433 supernatants (data not shown). This preparation has a specific activity of 117 units CA 125/ug of protein. The specific activity is determined by measuring the CA 125 activity using the Centocor CA 125 RIA kit and determining the amount of protein by amino acid analysis on this same lot of purified CA 125 antigen. Final fractionation of the antigen is accomplished by immunoaffinity on an immobilized OC125-Protein A-Sepharose Cl-4B column. The antigen which eluted from the column with diethylamine (DEA) has a specific activity of 317 units CA 125/ug of protein.

Figure 5:
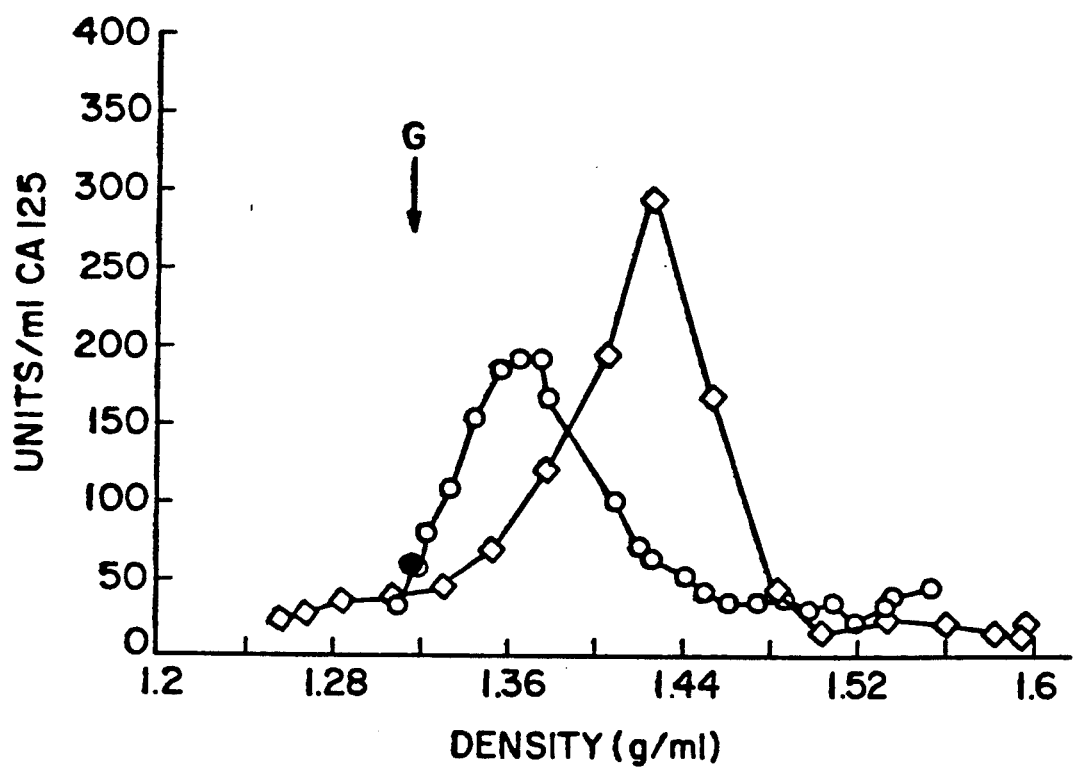
FIG. 5 shows density gradient ultracentrifugation of the CA 125 antigen isolated from OVCA 433 following partial purification on a Sepharose CL-4B column (  3  ) and following immunoaffinity purification on an immobilized OC125-Protein A-Sepharose CL-4B column (       )

Samples of antigen eluting from a Sepharose CL-4B column and from an OC125 immunoaffinity column were subjected to density gradient ultracentrifugation. This procedure reveals different average bouyant densities for the two antigen preparations (FIG. 5). The more highly purified DEA eluate has a bouyant density of approximately 1.36 g/ml whereas the bouyant density of the OVCA 433/4B is approximately 1.42 g/ml. This suggests that the less pure antigen is associated with more highly glycosylated proteins which would result in the polydisperse nature of the bouyant density profile as well as the higher average bouyant density observed.

Carboyhydrate Composition of the CA 125 Antigen Isolated by Affinity Chromatography Preliminary carbohydrate composition of OVCA 433/4B/DEA reveals that sialic acid, fucose, mannose, galactose, N-acetyl glucosamine, and N-acetyl galactosamine are present in the ratio 3.6:0.40:3.0:6.6:5.8:2.2, respectively (data not shown). This data suggests that there are both N- and O-linked oligosaccharides present. In addition, this immunopurified CA 125 antigen is found to contain 24% carboyhydrate, by mass, in close agreement with that calculated from its bouyant density of 1.36 g/ml. Therefore, the CA 125 antigen is not a typical mucin and does not have a significant amount, if any, of lipid associated with it.

Nature of the CA 125 Determinant

The nature of the CA 125 determinant was investigated using a number of chemical and physical treatments, as well as exhaustive exoglycosidase and protease digestions of the antigen. Periodate oxidation (Table I) of the CA 125 immunoreactive antigen isolated from OVCA 433/4B and from human milk/4B has no effect on activity at periodate concentrations and reaction times that totally destroyed activity of the CA 19-9 carbohydrate determinant, the sialylated lacto-N-fucopentaose II. In fact, at the lowest periodate concentrations which destroyed CA 19-9 activity (0.1 mM) there actually appears to be an increase in CA 125 activity. Only at very high concentrations of periodate (100 mM) or at very long reaction times (24 h) is there a significant decrease in CA 125 activity, which is likely due to non-specific oxidation of the antigen protein backbone.

TABLE I

EFFECT OF PERIODATE OXIDATION ON CA 125 ACTIVITY AT VARIOUS CONCENTRATIONS AND REACTION TIMES.

| SAMPLE | PERIODATE CONCENTRATION (mM) | CA 125 Activity (% Remaining) TIME (h) | | | |
|---|---|---|---|---|---|
| | | 0 | 3 | 6 | 24 |
| OVCA 433/ | 0 | 100 | 99 | 102 | 102 |
| PCA/4B | 0.1 | 100 | 110 | 115 | 92 |
| | 1.0 | 100 | 134 | 144 | 121 |
| | 10.0 | 100 | 151 | 135 | 119 |
| | 100.0 | 100 | 72 | 48 | 40 |
| Human milk/ | 0 | 100 | 101 | 103 | 98 |
| 4B | 0.1 | 100 | 103 | 93 | 97 |
| | 1.0 | 100 | 107 | 110 | 84 |
| | 10.0 | 100 | 111 | 69 | 50 |
| | 100.0 | 100 | 7 | 5 | 5 |
| Positive | 0 | 100 | 100 | 97 | 99 |
| Control | 0.1 | 100 | 16 | 11 | 5 |
| 19-9 cGP | 1.0 | 100 | 10 | 5 | 5 |

Chemical and physical treatments (Table II) which denature most proteins, that is, reduction and alkylation in 6M guanidine-HCl, 8M urea, and boiling all reduce the CA 125 immunoreactivity substantially. Reduction alone, however, does not seem to affect CA 125 immunoreactivity. Thus, the decrease in activity observed with either reduction of alkylation in the presence of guanidine-HCl is mainly the result of guanidine-HCl acting on the antigen. There is almost complete loss of activity with reduction and alkylation in the presence of guanidine-HCl. In addition, neither the anionic detergent SDS nor the non-ionic detergent NP-40 affects the CA 125 immunoreactivity.

TABLE II

THE EFFECT OF CHEMICAL TREATMENTS ON CA 125 ACTIVITY

| | CA 125 Activity (% Remaining) | | |
|---|---|---|---|
| Treatment | Plate Assay | Inhibition Assay | IRMA (Sandwich) |
| Control | 100 | 100 | 100 |
| Guanidine-HCl(6M, 45° 4 h) | ND | 20 | 49 |
| Reduction (10 mM DTT, 4 h, 45° C.) | ND | 73 | 98 |
| Reduction in guanidine-HCl | ND | 40 | 20 |
| Alkylation (20 mM iodoacetic acid, 30 min, 23° C.) | ND | 31 | 82 |
| Alkylation in guanidine-HCl | ND | 40 | 29 |
| Reduction and alkylation | ND | 53 | 51 |
| Reduction and alkylation in guanidine-HCl | 5 | 12 | 5-7 |
| Urea (8M, 24 h, 4° C.) | 100 | 100 | 100 |
| Urea (8M, 24 h, 45° C.) | 15 | 10 | 0 |
| Heat (100° C., 20 min.) | 0 | 0 | 0 |
| SDS (2%) | 100 | ND | 100 |
| NP-40 (10%) | 100 | ND | 100 |

ND designates assay was not done.

Various combinations of exoglycosidase treatments were performed on the CA 125 antigen (Table III). The solid-phase IRMA indicates only slight losses of CA 125 immunoreactivity either with α-galactosidase and/or β-galactosidase treatments. On the other hand, no loss of immunoreactivity is demonstrated using the plate assay. In fact, there is an increase in the ability of the immobilized antigen to bind radiolabeled OC125 antibody following most of the exoglycosidase treatments. This result corroborates that obtained with periodate oxidation, that is, removal of terminal carbohydrate moieties may actually increase access of OC125 to the CA 125 determinant.

Finally, exhaustive protease digestion with pronase, trypsin, or chymotrypsin causes complete loss of antigenic activity as measured with either the IRMA or the plate assays (Table III).

TABLE III
THE EFFECT OF ENZYMATIC DIGESTION ON CA 125 ANTIGEN ACTIVITY ISOLATED FROM OVCA 433

| | CA 125 Activity (% Remaining) | |
|---|---|---|
| | IRMA | Plate Assay |
| Exoglycosidase Treatment | | |
| Control | 100 | 100 |
| Neuraminidase (N) | 96 | 126 |
| N + α-Fucosidase (F) | 106 | 128 |
| N + F + β-Galactosidase(βG) | 96 | 129 |
| N + F + βG + Hexosaminidase | 109 | 123 |
| α-Galactosidase | 94 | 117 |
| α + β-galactosidase | 88 | 116 |
| Chondroitinase ABC | 93 | 94 |
| Exhaustive Protease Treatment | | |
| Pronase | 0 | 0 |
| Trypsin | 0 | 0 |
| Chymotrypsin | 0 | 0 |

DISCUSSION

The murine monoclonal antibody OC125 recognizes a human ovarian carcinoma-associated antigenic determinant (CA 125). We have isolated glycoprotein complexes from the ovarian cancer cell line OVCA 433, human serum, and human milk all of which express CA 125 determinant activity. In addition, we have evidence of CA 125 activity in seminal plasma which is in contrast to the observations of de Bruijn et. al. supra. Chemical treatment and chromatography of the high molecular weight complex isolated from OVCA 433 cell supernatants gave rise to a 200 kDa immunoreactive species. It is possible, however, that the actual protein which expressed the antigenic determinant may be of still lower molecular weight. Further attempts to isolate a lower molecular weight immunoreactive species have thus far proven ineffective. Moreover, the isolation scheme described here does not give rise to a completely homogenous and pure species.

The antigen expressing the CA 125 determinant isolated from several sources exists as a high molecular weight glycoprotein complex with an average bouyant density of between 1.36 and 1.46 g/ml. Moreover, these average densities indicated that each of the antigens isolated from three sources may have had a slightly different protein and carbohydrate composition. If a mucin is defined as a high molecular weight glycoprotein composed of 50% or more carbohydrate with a majority of O-linked oligosaccharides containing little ore no N-linked chains, then the CA 125 antigen is not a typical mucin. This conclusion is based on the CA 125 carbohydrate composition of 24%, the high amount of mannose present, the majority of N-linked oligosaccharides, and the CA 125 antigen bouyant density. The average bouyant density of unglycosylated protein is between 1.25 and 1.35 g/ml, while the average bouyant density of mucins is approximately 1.50 g/ml. This finding is in contrast to that reported for other epithelial tumor-associated antigens recognized by monoclonal antibodies such as 19-9 (Magnani, J. L. et. al., *J. Biol. Chem;* 257:14365–14369, 1982), B72.3 (Johnson, V. G. et. al., *Cancer Res.; b* 45:850–857, 1986), DU-PAN-2 (Lan, M. S. et. al., *Cancer Res;* 45:305–310, 1985), and F36/22 (Croghan, G. A. et. al.; *Cancer Res.* 43:4980–5988, 1983), all of which have been classified as high molecular weight mucin-like glycoproteins based on their higher bouyant densities.

The higher molecular weight antigen complex isolated from the supernatant of OVCA 433 was reactive with the monoclonal antibody 19-9 (Magnani et. al. supra,), suggesting that the CA 19-9 determinant is present on this complex. However, we have clearly shown by electrophoresis and immunoblotting that the CA 19-9 and the CA 125 determinants were not located on the same glycoprotein since the OC125 immunoaffinity purified CA 125 antigen showed no reactivity with the monoclonal antibody 19-9. This observation is contrary to that suggested by Hanisch et. al. supra who had isolated both CA 19-9 and CA 125 activity from human milk.

Chemical and physical treatments of CA 125 antigen were undertaken to better understand the nature of the antigenic determinant recognized by the monoclonal antibody OC125. Periodate oxidation of CA 125 reduced the immunoreactivity only at high concentrations of periodate or with prolonged reaction times. In fact, the activity of the antigen actually increased at concentrations and reaction times which caused total loss of immunoreactivity of the CA 19-9 determinant. Non-specific oxidation of the protein backbone probably caused the loss of CA 125 activity at higher concentrations of periodate. During CA 125 antigen purification, there was a loss of 82% of the original activity following urea and heat treatment. This apparent loss in activity was most likely due to breakdown of antigen complex to a less aggregated form or to partial denaturation of the antigen. A lower aggregated state may lead to a lower unit value as the CA 125 RIA is sensitive to CA 125 antigen valency, i.e. the number of OC125 binding sites per antigen molecule.

The observations of Hanisch et. al. supra which suggested that the CA 125 determinant is carbohydrate in nature were based on two criteria; its sensitivity to periodate oxidation (at a concentration of 100 mM and a reaction time of 18 h), and its loss of activity under conditions which would selectively cleave N-acetylneuraminic acid (pH 3.3, 100° C.). Their results also indicated that neuraminidas treatment alone caused only slight reduction of immunoreactivity even though approximately 97% of the mucin-linked sialic acid was cleaved. Our results clearly show that concentrations of periodate sufficient to oxidize carbohydrates do not affect CA 125 activity. It is not surprising, therefore, that pH 3.3 at 100° C. destroyed CA 125 antigenic activity In addition, greater than 95% of the activity was lost upon reduction and alkylation treatment in the presence of guanidine-HCl. Lastly, exoglycosidase treatments actually caused an increase in CA 125 activity while antigen activity was completely eradicated with exhaustive protease digestion. These data strongly suggest that the CA 125 determinant is proteinaceous in nature, or at the very least, is protein associated with carbohydrate in a conformationally dependent epitope This may explain the similarity of the antigen isolated from the various sources such as human serum, OVCA 433, and human milk. A peptide determinant would be expected to be more highly conserved than a carbohydrate determinant, that is, a protein sequence is more likely to be associated with a single unique protein, whereas a carbohydrate structure may exist on several different proteins. These results may not be completely unique as the nature of the tumor associated glycoprotein epitope (TAG-72) recognized by the monoclonal antibody B72.3 seemed to indicate protein, in addition to carbohydrate, as forming part of the conformationally dependent TAG-72 determinant.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A preparation of an isolated immunoreactive CA 125 antigen which is a glycoprotein having a molecular weight of about 200 kDa as determined by SDS:PAGE chromatography, and having a carbohydrate composition of about 24% by mass, and which preparation is reactive with the monoclonal antibody OC 125 but is free of reactivity with monoclonal antibody 19-9.

2. A preparation of an isolated, immunoreactive CA 125 antigen having the following characteristics:
   a. a molecular weight of about 200 kDa;
   b. a buoyant density of about 1.36 g/ml;
   c. a carbohydrate composition of about 24% by mass;
   d. a carbohydrate composition of sialic acid, fucose, mannoase, galactose, N-acetylglucosamine, and N-acetyl galactosamine in a ratio of abut 3.6/0.4/3.0/6.6/5.8/2.2; and
   e. reactivity with the antibody OC 125, but is free of reactivity with monoclonal antibody 19-9.

3. An immunogen composition for immunizing an animal against CA 125 antigen comprising a preparation of an isolated CA 125 antigen which is a glycoprotein having a molecular weight of about 200 kDa as determined by SDS:PAGE chromatography and having a carbohydrate composition of about 25% by mass, and which is reactive with antibody OC 125 but is free of reactivity with monoclonal antibody 19-9, in a physiologically acceptable vehicle.

4. A process for the production of antibodies against CA 125 comprising immunization with the immunogenic composition of claim 3.

5. A method for isolating the antigen CA 125, comprising the steps of:
   a. obtaining the cell culture medium from a culture of cells which shed CA 125 into the medium;
   b. subjecting the medium to acid precipitation to provide an acid soluble and an acid insoluble fraction;
   c. recovering and neutralizing the acid soluble fraction;
   d. separating the CA 125 species in the acid soluble fraction from lower molecular weight components of the fraction by molecular exclusion chromatography and recovering the CA 125 species;
   e. treating the recovered CA 125 species with a chaotropic agent to disrupt high molecular weight CA 125 species;
   f. separating the lower molecular weight CA 125 species by molecular exclusion chromatography in the presence of the chaotropic agent;
   g. recovering the eluted fraction containing CA 125 species;
   h. contacting the CA 125 species with an immunoadsorbent comprising an antibody which binds CA 125 coupled to a resin under condition which permits selective adsorption of CA 125 by the immunoadsorbent; and
   i. recovering the CA 125 from the immunoadsorbent.

6. A method of claim 5, wherein the cells which shed CA 125 antigen are ovarian carcinoma cells.

7. A method of claim 6, wherein the acid precipitation is performed with perchloric acid.

8. A method of claim 7, wherein the molecular size exclusion chromatography of step d is performed on Sepharose 4B-CL resin.

9. A method of claim 8, wherein the chaotropic agent is urea or quanidine-HCl.

10. A method of claim 9, wherein the molecular size exclusion chromatography of step f is performed on Sepharose 6B resin.

11. A method of claim 10, wherein the chaotropic agent is separated form the CA 125 species by dialysis after the molecular size exclusion chromatography.

12. A method of claim 11, wherein the antibody which binds to CA 125 is the OC 125 antibody.

13. A method of isolating CA 125, comprising the steps of:
   a. obtaining a cell-free supernatant from a culture of ovarian carcinoma cells;
   b. acidifying the supernatant to precipitate protein;
   c. separating the precipitated protein from the acid soluble fraction of the supernatant;
   d. neutralizing the soluble fraction;
   e. separating the high molecular weight CA 125 of 1000 kD and greater from the smaller molecular weight CA 125 species and from other components in the soluble fraction by molecular size exclusion chromatography;
   f. treating the high molecular weight CA 125 species with urea to disrupt the high molecular weight species;
   g. separating the CA 125 species by molecular exclusion chromatography on a resin which retains molecules in the 200 kD range in the presence of urea; and
   h. immunopurifying the CA 125 species.

14. A method of claim 13, wherein the ovarian carcinoma cells are selected from the group consisting of OVCA 433, NIH: OVCAR-3, SK-OV-3, CAOV-3 and CAOV-4.

15. A method of claim 13, wherein the cells are OVCA 433.

16. A method of claim 13, wherein the supernatant is acidified with perchloric acid.

17. A method of claim 13, wherein the molecular size exclusion chromatography of step e is performed on Sepharose 4B-CL resin.

18. A method of claim 13, wherein the urea is about 6 molar.

19. A method of claim 13, wherein the molecular size exclusion chromatography of step g is performed on Sepharose B resin.

20. A method of isolating CA 125 species of about 200 kD molecular weight, comprising the steps of:
   a. obtaining a cell free supernatant from a culture of ovarian carcinoma cells which shed CA 125 into the culture medium;
   b. acidifying the supernatant with perchloric acid to precipitate protein;
   c. removing precipitated protein and neutralizing the acid soluble fraction;
   d. submitting the neutralized acid soluble fraction to molecular size exclusion chromatography on Sepharose CL-4B resin and recovering from the column the void volume fraction containing CA 125 activity;

e. treating the fraction containing CA 125 activity with urea at about 6M;

f. submitting the urea treated fraction to molecular size exclusion chromatography on Sepharose CL-6B in a buffer controlled with Urea 6M and about 1% SDS and recovering the eluted fraction containing CA 125 activity;

g. removing the urea from the recovered fraction;

h. applying the fraction to an immunoaffinity column comprising OC 125 antibody coupled to protein A Sepharose via dimethylpimelimidate i. eluting the CA 125 from the immunoaffinity column with diethylamine.

* * * * *